United States Patent [19]

Romero-Sierra et al.

[11] 4,272,571

[45] Jun. 9, 1981

[54] FLOWER PRESERVATION

[75] Inventors: Cesar Romero-Sierra, Bath; John C. Webb, Kingston, both of Canada

[73] Assignee: Queen's University at Kingston, Kingston, Canada

[21] Appl. No.: 45,126

[22] Filed: Jun. 4, 1979

Related U.S. Application Data

[63] Continuation-in-part of Ser. No. 914,172, Jun. 9, 1978, abandoned.

[51] Int. Cl.³ .............................................. A01L 3/00
[52] U.S. Cl. ............................... 428/24; 252/400 A; 252/400 R; 252/407; 71/68; 47/DIG. 2; 252/402; 252/403; 427/4
[58] Field of Search ................. 427/4; 47/DIG. 2, 11; 252/400 A, 400 R, 401–403, 405, 407; 71/68; 428/22, 24

[56] References Cited

U.S. PATENT DOCUMENTS

| | | | |
|---|---|---|---|
| 2,168,304 | 8/1939 | Meyr | 71/68 |
| 2,567,929 | 9/1951 | Fessenden | 427/4 |
| 3,104,968 | 9/1963 | Fisher | 71/68 |

FOREIGN PATENT DOCUMENTS

| | | | |
|---|---|---|---|
| 1562314 | 2/1969 | France | 71/68 |

*Primary Examiner*—Sam Silverberg
*Attorney, Agent, or Firm*—Richard J. Hicks; Stanley E. Johnson

[57] ABSTRACT

A process for preserving substantially any variety of flower while retaining the natural colors thereof, in which the flower is immersed in an essentially water-free composition comprising: at least one dehydrating alcohol, a carboxylic acid, a urea-containing compound, an alkaline citrate, and zero to an effective amount of at least one of a silicone fluid, a silicone resin, an alkaline formaldehyde sulfoxylate, aluminum or magnesium sulphate and cupric or other transitional metal sulphate for sufficient time to dehydrate the flower, said composition also containing a sufficient quantity of at least one compound in the group consisting of an alkaline phosphate, a lower carboxylic acid and phenol so as to ensure that the composition has a pH in the range 5–7. Following immersion the flower is dried and, if desired coated with a silicone resin.

16 Claims, No Drawings

FLOWER PRESERVATION

This application is a continuation-in-part of our earlier filed application Ser. No. 914,172 filed June 9, 1978 and now abandoned.

This application relates generally to the preservation of flowers and more particularly to a process and novel composition of matter for the preservation of the natural colours of flowers, and to the preserved flower product.

The preservation of flowers for museum specimens, for educational purposes in the natural sciences and elsewhere, for decorative and ornamental use, for displays and the like has been practised for many years and many processes for such preservation have been described in the literature. Attention is particularly directed to U.S. Pat. Nos. 2,658,929; 2,658,836 and 3,698,809 to Fessenden and U.S. Pat. No. 2,971,292 to Malecki and to "Handbook of Plastic Embedding" E. L. Lutz (1969) P. 60–73 for descriptions of the processes employed heretofore for the preservation of flowers and other plant and animal tissues. Such prior art processes are not, however, entirely satisfactory because the delicate natural colours of the flowers tend to fade relatively quickly and the flowers are also extremely brittle, fragile and highly susceptible to damage in extremes of temperature or humidity so that special handling and storage techniques are necessary. Without such special techniques the natural beauty of the flowers is quickly lost and the flowers lose their usefulness for display or educational purposes. Indeed, storage in sealed bells or embedding in plastic have heretofore been the only practical methods of storage and handling. Further, in order to treat differently coloured flowers according to the prior art it has been found necessary to use a variety of treatment solutions as no single treatment solution, which is suitable for all colours of flowers, has evolved.

It is, therefore, an object of the present invention to provide a process and a single composition of matter for the preservation of flowers which is suitable for use with substantially all colours and varieties of flowers and which will result in naturally coloured flowers which retain the freshness, flexibility and beauty for relatively long periods of time without the necessity of special handling and storage techniques.

By one aspect of this invention there is provided an essentially water-free composition, for the preservation of fresh naturally coloured blooms, consisting essentially of at least one dehydrating alcohol, a urea-containing compound, a carboyxlic acid, an alkaline citrate, and from zero to an effective amount of at least one of: aluminum or magnesium sulphate, a silicone fluid, a silicone resin, a transitional metal sulphate, and an alkaline formaldehyde sulfoxylate, said composition also containing a sufficient quantity of at least one compound of the group consisting of an alkaline phosphate, a lower carboxylic acid and phenol so as to ensure that said composition has a pH in the range 5 to 7.

Thus, by a preferred aspect of this invention there is provided a composition for the preservation of naturally coloured plant tissues comprising, in amounts per liter:
700–900 ml. of at least one dehydrating alcohol
6–8 g. alkaline phosphate
0–3 g. alkaline formaldehyde sulfoxylate
2.5–7.5 g. citric acid
10–20 g. thiourea
0–10 g. aluminum sulphate
3–12 g. alkaline citrate
0–2 g. cupric sulphate
10–200 ml. silicone fluid
0–50 ml. silicone resin, and
0–62 ml. phenol.

By another aspect there is provided a process for preserving fresh, naturally coloured blooms comprising immersing said blooms in an essentially water-free composition comprising at least one dehydrating alcohol, a urea-containing compound, a carboxylic acid, an alkaline citrate, and from zero to an effective amount of at least one of aluminum or magnesium sulphate, a silicone fluid, a silicone resin, a transitional metal sulphate, and an alkaline formaldehyde sulfoxylate, said composition also containing a sufficient quanity of at least one compound of the group consisting of an alkaline phosphate, a lower carboxylic acid and phenol so as to ensure that the composition has a pH in the range 5 to 7, for a period of time sufficient to effect substantially complete dehydration, and subsequently drying at substantially room temperature.

By another preferred aspect of this invention there is provided a process for preserving naturally coloured plant tissues comprising immersing said tissues in a composition comprising:
450–900 ml. of at least one dehydrating alcohol
6–8 g. alkaline phosphate
0–3 g. alkali metal formaldehyde sulfoxylate
2.5–7.5 g. citric acid
10–20 g. thiourea
0–10 g. aluminum sulphate
3–12 g. alkali metal citrate
0–2 g. cupric sulphate
10–200 ml. silicone fluid
0–50 ml. silicone resin, and
0–62 ml. phenol,
removing said tissues from said composition and drying at substantially room temperature.

We have found that all blooms, substantially regardless of colour with the exception of the green parts thereof, can be successfully treated according to the invention by soaking, as described in more detail hereinafter, in a composition comprising (to make 1 liter):
175–575 ml. tertiary butyl alcohol
100–300 ml. 1-propanol
200–400 ml. 2-propanol
6–8 g. sodium phosphate
0–3 g. sodium formaldehyde sulfoxylate
2.5–7.5 g. citric acid
10–20 g. thiourea
0–10 g. aluminum sulphate
3–12 g. sodium citrate
0–2 g. cupric sulphate
10–200 ml. silicone fluid
0–50 ml. silicone resin, and
0–62 ml. phenol (88%).

Variations of constituents within the above ranges are possible and even desirable for treatment of particularly coloured blooms as will be discussed in more detail hereinafter. A "universal" composition, however, which has been found effective for virtually all colours and blooms and which is clearly advantageous as it simplifies inventory and stock control and is particularly suitable for sale as a consumer-product, comprises (per liter):
375 ml. tertiary butyl alcohol 200 ml. 1-propanol
300 ml. 2-propanol
12 g. sodium phosphate
2 g. sodium formaldehyde sulfoxylate
5 g. citric acid
10 g. thiourea
5 g. aluminum sulphate
6 g. sodium citrate
1 g. cupric sulphate
63 ml. silicone fluid
25 ml. silicone resin, and
37 ml. phenol (88%).

The invention will be described in more detail hereinafter with reference to the specific examples. It will be appreciated that there are three objectives of the treatment according to the present invention (a) dehydration of the blooms, (b) preservation of colour, and (c) protection of treated blooms.

It is known that in order to preserve a bloom all water must be eliminated from the bloom. It is also known that many monohydric alcohols, and in particular tertiary butyl alcohol, are extremely efficient dehydrating agents. Although any one or more such dehydrating alcohols may be used we have found that a mixture of tertiary butyl alcohol, 1-propyl alcohol and 2-propyl alcohol is particularly effective for the treatment of flowers. The tertiary butyl alcohol (all proportions hereinafter are per liter of treating composition, unless otherwise stated) can vary from 175 ml. to 575 ml. with a preferred concentration of about 375 ml. Generally, the more tertiary butyl alcohol relative to the other two alcohols, the shorter the period of time of immersion and vice versa. The dehydrating properties of tertiary butyl alcohol are so considerable that the final product bloom tends to be brittle if not compensated by the inclusion of a silicone fluid, such as Microfil (Registered Trademark) MV-diluent, in the formulation. The upper limit of tertiary butyl alcohol, relative to the 1-propanol and 2-propanol is controlled at least in part by the fact that tertiary butyl alcohol freezes at 24° C.

The 1-propanol and 2-propanol components are in themselves effective dehydrants and tend to modify the harsh effects of tertiary butyl alcohol used above, without interferring with its effectiveness. The amount of these components is not critical to the formulation provided modifications to the other components are also made.

Sodium phosphate dibasic or other alkaline phosphate, such as potassium or ammonium phosphate is preferably added to the formulation to control or buffer the pH. It has been found that pH control of the formulation is necessary for consistent results and preferably the pH should be in the range 6.0–6.5. If no green is present in the bloom to be treated the pH may be as low as 5 and pH 7 is preferred for the treatment of green. It will, of course, be appreciated that most blooms to be treated will include a green stem and for this reason alone the preferred pH will be in the range 6.0–6.5. We have found, however, that, depending upon the exact formulation employed and the number and composition of the optional constituents present, pH control can be achieved even without the use of an alkaline phosphate buffer provided a sufficient quantity of a lower carboxylic acid such as propionic acid and/or phenol is added.

Sodium or other alkaline formaldehyde sulfoxylate is optionally added to the formulation for its bridging properties and is particularly useful in the treatment of white blooms. It tends to speed up the setting of the colour and although omission thereof does not cause any essential change in results, the overall quality of the preserved blooms, especially white blooms is reduced.

A carboxylic acid is employed primarily as a colour preservative for red, pink, yellow and white. Although suitable acids include tartaric acid, salicylic and carbolic acid, citric acid is preferred. Although the amount can be varied widely between the limits described hereinabove, a carboxylic acid such as citric acid cannot be eliminated. Too low a concentration causes the colours to appear faded, especially in red flowers. Too high a concentration can cause burning or colour changes, particularly in the green portions of the flower.

A urea-containing compound is an essential constituent to prevent loss of pigments from the blooms and, when used together with citric acid and sodium citrate, it increases the efficiency of those chemicals and prolongs the active life of the composition. Thiourea is a preferred urea-compound. Insufficient thiourea or other urea-containing compound causes the colours to appear dead and lacking in their original fresh beauty, and some colours may even change completely, as for instance a blue orchid may turn a sickly red or pink. Excessive thiourea is not believed to have any deleterious effect except to increase the cost of the formulation.

Aluminum sulphate is an optional constituent in the formulation which appears to affect the overall quality of the colours of the blooms. Too much aluminum sulphate (more than 100% excess) may cause spots resembling burns on red and blue petals. Magnesium sulphate may also be employed but tends to be hydroscopic.

Sodium or other alkaline citrate is added as a colour preservative for blue, purple and orange blooms and is used in conjunction with thiourea. Omission of sodium citrate causes the colours to appear faded. Excess sodium citrate does not appear to affect blue, purple or orange blooms but red and pink blooms are adversely affected.

Cupric or other transitional metal (Fe, Ni) sulphate is an optional constituent added not only to fix the colour of the blooms but also to draw away moisture which gathers at the bottom of the treatment tank through repeated treatment of the blooms, thereby extending the life of the composition. Excess of cupric sulphate tends to fall to the bottom of the tank undissolved but there is some risk of burns to the blooms.

A silicone fluid, such as a silicone rubber injection compound sold under the registered trademark Microfil (MV-diluent) by Canton Biomedical Products Inc. of Boulder, Colo. or dimethyl siloxane polymer sold under the registered trademark Dow Corning 200 by Dow Chemical Corp., is preferably added to the formulation to fulfil the third objective of the treatment, namely to protect the final product from humidity and temperature. The silicone fluid also has the effect of reducing the brittleness of the bloom caused by the use of the alcohol dehydrating agents. The silicone fluid impregnates the tissue of the blooms as it is being preserved and also tends to strengthen the petaltorus junction. Reduction of the silicone fluid below about 30 ml./l. results in inferior products, from the point of view of biological stress, but an excess of the silicone fluid has no effect and merely increases the cost of the formulation.

In order to further protect the preserved bloom against the humidity and improve the water repellancy thereof a silicone polymer such as Microfil MV-132 Clear (registered trademark) sold by Canton Biomedical Products Inc. or SYL-OFF Registered Trademark, Dow Corning Fluid 1107, may be incorporated. It is stressed that neither the silicone fluid or polymer play any part in the colour preservation of the blooms but they do affect the physical and biological properties involved in the resistance of the blooms to withstand mechanical and environmental stresses, essentially rough handling, humidity and temperature.

Phenol and/or a lower carboxylic acid may be added to the formulation to enhance the efficiency of the other constituents. They appear to act as pH buffers, as dehydrating agents and to aid in locking in the colours. The preferred lower carboxylic acid is propionic acid, which is frequently present in biological tissue, although other acids such as acetic or butyric acid may also be employed. There are, however, disadvantages accruing to the use of such other acids: the range of acetic acid is very limited and an excess tends to "burn" the bloom very easily, and butyric acid has an objectionable smell which is frequently difficult or impossible to eliminate from the treated bloom. The amount of phenol and/or propionic acid to be added depends upon the result desired and upon the quantity of other additives in the solution. Not only do the phenol and/or propionic acid act as a buffer but also they affect the colour balance, particularly reds, in the bloom. For example, propionic acid tends to darken a red bloom while phenol tends to lighten a red bloom. A mixture of propionic acid and phenol tends to make the colour more vivid. It is stressed that many of the solid compounds in the formulation are insoluble or only sparingly soluble in the organic liquids in the composition and tend to settle out. It is improper, therefore, to refer to "a solution" which would imply complete dissolution. Although not wishing to be bound by this explanation it is believed that the solid compounds enter solution by way of the water extracted from the blooms as dehydration thereof proceeds, as explained in more detail hereinafter.

The process to treat the blooms according to the present invention is quite simple and straightforward. A fresh bloom is chosen and a floral wire is inserted into the stem or bloom and a weight is added to keep the bloom submerged in the composition. The composition, formulated as described hereinabove is contained in a suitable bath or container at a temperature in the range of about 45°-75° F. The bloom is left suspended in the bath for from 6 to 24 hours without any agitation, depending upon size and water content of the bloom and the freshness of the solution. Upon immersion in the composition, substantially all colour appears to disappear from the petals as dehydration occurs under the action of the dehydrating alcohols. The colour slowly returns to the normal pre-treatment level as the solid colour fixers and the like take up the extracted water and actively enter solution, thus giving a useful indication of the treatment time required. Large, fleshy blooms require longer periods of immersion and care must be taken to ensure the bloom is immersed sufficiently long to treat the relatively heavy and impervious torus. Following the immersion treatment the bloom is removed from the composition and air dried at room temperature and relatively low humidity for 8 to 10 hours. Blooms thus treated can generally be stored and displayed without further treatment for relatively long periods of time (of the order of 4–6 months at least) provided the temperature and humidity conditions are suitable (i.e. up to about 80° F. and 60–70% relative humidity). More stressful environmental conditions require that the blooms be stored in sealed glass domes, where they will likely last for years, or be further coated. It has been found that dipping or spraying with a conformal coating resin, such as Dow Corning R43117 Silicone Resin alone or diluted with Dow Corning Fluid 200 (Registered Trademark) (at 0.65 centistokes) or any other diluent, is satisfactory for this purpose. Preferably the coating is applied by dipping the bloom into the resin thinned with a diluent such as xylene at a temperature in the range 50°-80° F. for a few minutes. The coated bloom is then dried at room temperature for several hours to cure the resin coating. The resin cures to a clear shiny coating and leaves the bloom relatively pliable. The shiny surface is often desirable but if a matte surface is desired this can be sprayed on with any one of a number of known finishes. The thickness of the coating has a bearing on the appearance of the bloom—thin coatings lend a natural and delicate appearance to the bloom, while thick coatings make for sturdy blooms often of special beauty. After a coating treatment as described herein, roses and geraniums for example, have been exposed to light equal to several million foot-candle-hours, 95% humidity and temperatures up to 85° F. with only slight colour fading. Under more normal conditions the colours remain unaltered.

EXAMPLE 1

A series of preserving compositions were prepared using mixtures of tertiary butyl alcohol, 1-propanol and 2-propanol to which the following components were added and at least partially dissolved, in sequence so as to maintain the pH of the composition throughout mixing in the range 6–6.5: dibasic sodium phosphate, sodium formaldehyde sulfoxylate, citric acid, thiourea, aluminum sulphate, sodium citrate, cupric sulphate, Microfil* Mv-diluent, Mircofil* Mv-132 Clear, propionic acid and phenol, in amounts per liter as set forth in Table I:

*Microfil is a Registered Trademark

TABLE I

| Component | Comp. A | Comp. B | Comp. C | Comp. D | Comp. E | Comp. F | Comp. G | Comp. H | Comp. J |
|---|---|---|---|---|---|---|---|---|---|
| tertiary butyl alcohol (ml.) | 375 | 375 | 375 | 375 | 375 | 375 | 375 | 375 | 375 |
| 1-propanol (ml.) | 200 | 200 | 200 | 200 | 200 | 200 | 200 | 200 | 200 |
| 2-propanol (ml.) | 300 | 300 | 300 | 300 | 300 | 300 | 300 | 300 | 300 |
| sodium phosphate (g.) | 12 | — | 12 | 12 | 12 | 12 | 12 | 12 | 12 |
| sodium formaldehyde sulphoxalate (g.) | 2 | 2 | 4 | 2 | 2 | 2 | 2 | 2 | 2 |
| citric acid (g.) | 5 | 5 | 5 | 10 | 5 | 5 | 5 | 5 | 5 |
| thiourea (g.) | 10 | 10 | 10 | 10 | 5 | 20* | 10 | 10 | 10 |
| aluminum sulphate (g.) | 5 | 5 | 5 | 5 | 5 | 5 | 10 | 2.5 | 5 |
| sodium citrate (g.) | 6 | 6 | 6 | 6 | 6 | 6 | 6 | 6 | 3 |
| cupric sulphate (g.) | 1 | 1 | 1 | 1 | 1 | 1 | 1 | 1 | 1 |
| Microfil-MV-diluent (ml.) | 63 | 63 | 63 | 63 | 63 | 63 | 63 | 63 | 63 |
| Microfil-132 Clear (ml.) | 25 | 25 | 25 | 25 | 25 | 25 | 25 | 25 | 25 |

TABLE I-continued

| | | | | | | | | | |
|---|---|---|---|---|---|---|---|---|---|
| Phenol (88%) (ml.) | 37 | 37 | 37 | 37 | 37 | 37 | 37 | 37 | 37 |
| Propionic Acid (ml.) | — | — | — | — | — | — | — | — | — |

| Component | Comp. K | Comp. L | Comp. M | Comp. N | Comp. P | Comp. Q | Comp. R | Comp. S |
|---|---|---|---|---|---|---|---|---|
| tertiary butyl alcohol (ml.) | 375 | 375 | 375 | 375 | 375 | 375 | 375 | 666 |
| 1-propanol (ml.) | 200 | 200 | 200 | 200 | 200 | 200 | 200 | 153 |
| 2-propanol (ml.) | 300 | 300 | 300 | 300 | 300 | 300 | 300 | 77 |
| sodium phosphate (g.) | 12 | 12 | 12 | 12 | 12 | 12 | 12 | — |
| sodium formaldehyde sulphoxalate (g.) | 2 | 2 | 2 | 2 | 2 | 2 | 2 | — |
| citric acid (g.) | 5 | 5 | 5 | 5 | 5 | 5 | 5 | 6.4 |
| thiourea (g.) | 10 | 10 | 10 | 10 | 10 | 10 | 10 | 10.4 |
| aluminum sulphate (g.) | 5 | 5 | 5 | 5 | 5 | 5 | 5 | — |
| sodium citrate (g.) | 12* | 6 | 6 | 6 | 6 | 6 | 6 | 6.4 |
| cupric sulphate (g.) | 1 | 0.5 | 2* | 1 | 1 | 1 | 1 | — |
| Microfil-MV-diluent (ml.) | 63 | 63 | 63 | 63 | 63 | 80 | 63 | — |
| Microfil-132 Clear (ml.) | 25 | 25 | 25 | 25 | 25 | 25 | 50 | — |
| Phenol (88%) (ml.) | 37 | 37 | 37 | 19 | 62 | 37 | 37 | — |
| Propionic Acid (ml.) | — | — | — | — | — | — | — | 102 |

*Not all chemical would dissolve.

EXAMPLE 2

Red roses, white and yellow chrysanthemums, blue and red fuchsia, yellow and pink hibiscus, red flowering maple, blue african violet and white and red geraniums were each preserved in each of compositions A-S as set forth in Table I hereinabove. The stems of individual blooms were wired and the blooms suspended in the preserving compositions at room temperature (45°-70° F.) for periods ranging from 6-24 hours depending on the size and water content of the bloom and the freshness of the preserving composition. In some cases it was necessary to attach a weight to the wire to ensure total immersion of the bloom in the composition. After the immersion treatment the blooms were removed from the composition and air dried at relatively low humidity (preferably less than 50%) for 8 to 10 hours. If higher humidities are encountered it may be necessary to take special steps to avoid reabsorption of water, such as by immersion in a resin such as Dow Corning R43117 with a solvent such as xylene. In some instances the dried blooms were subsequently coated with a coating or spray of a silicone resin at 50°-80° F. The results are set forth in Table II.

TABLE II

| | Flowers | | | | | | | | | | |
|---|---|---|---|---|---|---|---|---|---|---|---|
| Solution | red rose | white mum | yellow mum | blue fuschia | red fuschia | yellow hibiscus | pink hibiscus | red maple | blue African violet | white geranium | pink geranium |
| A | good colour | good colour | good colour | good colour | good colour | good colour | good colour | good colour | good colour | good colour | good colour |
| B | | | | retained colour - but pale and lacking "health" | | | | | | | |
| C | faded | good | faded white spots | faded | faded | faded white spots | faded | faded | faded | good | faded |
| D | good | good | some fading | damaged | good | some fading | good | good | damaged | good | good |
| E | pale | pale | pale | pale | pale | pale | pale | pale | very pale | pale | pale |
| F | good | good | good | good | good | good | good | good | good | good | good |
| G | spotty | good | good | spotty | spotty | good | spotty | spotty | spotty | good | spotty |
| H | good | good | good | good | good | good | good | good | good | good | good |
| J | good | good | good | faded | good | good | good | good | faded | good | good |
| K | good | good | good | good | good | good | good | good | good | good | good |
| L | | | | | good but stems turned light green | | | | | | |
| M | good | good | good | good | good | good | good | good | good | good | good |
| N | lost strength of colour | good | lost strength of colour | good | lost strength of colour | lost strength of colour | good | lost strength of colour | good | good | good |
| P | enhanced colour | good | good | good | enhanced colour | good | enhanced colour | enhanced colour | good | good | good |
| Q | | | | | good but slowed dehydration time | | | | | | |
| R | | | | | good but slow dehydration time | | | | | | |
| S | good | good | good | fair | fair | — | — | — | fair | good | good |

From Table II it can be seen that composition A is a preferred composition for universal use. Modifications thereto can, of course, be made for treatment of specifically coloured blooms. Thus, elimination of sodium phosphate (Composition B) results in relatively anemic flowers of all colours, additional sodium formaldehyde sulphoxalate (Composition C) is deleterious to yellow, red and blue flowers but appears beneficial to white flowers. Increasing citric acid (composition D) damages blue violets and fades yellows but enhances red flowers. Decreasing thiourea (Composition E) fades all colours to some extent but in particular dark blue violets, while increasing thiourea (Composition F) serves no useful purpose. Increasing aluminum sulphate (Composition G) causes spotty red and blue flowers as it appears to cause a burning in the cellular structure of the petals, reduction of aluminum sulphate (Composition H) has little noticeable effect. Reduction of sodium citrate (Composition J) causes fading of the blues and increasing sodium citrate (Composition K) has no noticeable effect as most of the increase appears not to dissolve. Reduction of cupric sulphate (Composition L) has little effect on the blooms but turned the stems light in colour, while increasing cupric sulphate (Composition M) merely resulted in undissolved chemical without effect on the blooms. It is believed however that excess cupric sulphate improves the aging properties of the solution as it appears to draw water from the alcohols. Reducing phenol (Composition N) faded both red and yellow flowers and excess phenol (Composition P) enhanced all blooms, especially red up to about 62 ml./l. but amounts in excess of this caused darkening indicating a burning effect. Additional silicone oil or resin (Compositions Q and R) has little effect on the colour or texture of any of the blooms but lengthened the dehydrating times, due, it is believed, to the isolating properties of these compounds.

Composition S differs from any of the preceding compositions in that the Microfil has been entirely eliminated, resulting in somewhat more fragile blooms which require more protection against biological stresses but which retain good colour and are suitable for display in a protected environment, such as by embedding. Another feature of composition S is the absence of the sodium phosphate buffer, in view of the elimination of sodium formaldehyde sulphoxalate, aluminum sulphate, cupric sulphate and phenol, and the replacement thereof by propionic acid.

It will be appreciated that many modifications to composition and process of the present invention may be effected by those skilled in the art without departing from the scope and ambit thereof. For example, it has been found possible to add the dehydrating alcohol or alcohols to a mixture of the other components of the composition, with excellent results. This is advantageous from the point of view of marketing and transportation as the bulk of the composition comprises the alcohol component and it may be preferable to obtain a suitable alcohol locally and mix it with a suitably packaged mixture of the remaining constituents. If scented blooms are desired it is, of course, a simple matter to incorporate a desired fragrance in the treatment composition or to spray the treated bloom therewith. As pointed out hereinabove, the use of butyric acid in the treatment solution should be avoided when a fragrant bloom is desired.

We claim:

1. An essentially water-free composition, for the single step preservation of fresh, naturally coloured, blooms comprising at least one dehydrating alcohol, a urea-containing compound, a carboxylic acid, and an alkaline citrate, an effective amount of at least one of: aluminum or magnesium sulphate, a transitional metal sulphate, and an alkaline formaldehyde sulfoxylate, and zero to an effective amount of at least one of a silicone fluid and a silicone resin and which also contains a sufficient quantity of at least one compound of the group consisting of an alkaline phosphate, a lower carboxylic acid and phenol so as to ensure said composition has a pH in the range 5 to 7.

2. A water-free composition, for the preservation of fresh, naturally coloured blooms, as claimed in claim 1 wherein said urea-containing compound is thiourea; said carboxylic acid is citric acid, said transitional metal sulphate is cupric sulphate, and said lower carboxylic acid is propionic acid.

3. A composition as claimed in claim 2 comprising, in amounts per liter:
   700–900 ml. of at least one dehydrating alcohol
   6–8 g. alkali phosphate
   0–3 g. alkali formaldehyde sulfoxylate
   2.5–7.5 g. citric acid
   10–20 g. thiourea
   0–10 g. aluminum sulphate
   3–12 g. alkali citrate
   0–2 g. cupric sulphate
   10–200 ml. silicone fluid
   0–50 ml. silicone resin
   0–62 ml. phenol.

4. A composition, as claimed in claim 3, comprising:
   175–575 ml. tertiary butyl alcohol
   100–300 ml. 1-propanol
   200–400 ml. 2-propanol
   6–8 g. sodium phosphate
   2–3 g. sodium formaldehyde sulfoxylate
   2.5–7.5 g. citric acid
   10–20 g. thiourea
   2.5–10 g. aluminum sulphate
   3–12 g. sodium citrate
   0.5–2 g. cupric sulphate
   10–200 ml. silicone fluid
   0–50 ml. silicone resin
   37–62 ml. phenol.

5. A composition as claimed in claim 1, wherein said silicone fluid is present in an amount of at least 30 ml./l.

6. A composition as claimed in claim 1, comprising:
   375 ml. tertiary butyl alcohol
   200 ml. 1-propanol
   300 ml. 2-propanol
   12 g. sodium phosphate
   2 g. sodium formaldehyde sulfoxylate
   5 g. citric acid
   10 g. thiourea
   5 g. aluminum sulphate
   6 g. sodium citrate
   1 g. cupric sulphate
   63 ml. silicone fluid
   25 ml. silicone resin
   37 ml. phenol.

7. A single step process for preserving fresh, naturally coloured blooms comprising immersing untreated said fresh blooms in an essentially water-free composition consisting essentially of at least one dehydrating alcohol, a urea-containing compound, a carboxylic acid, and an alkaline citrate, an effective amount of at least one of aluminum or magnesium sulphate, a transitional metal sulphate, and an alkaline formaldehyde sulfoxylate and from zero to an effective amount of at least one of a silicone fluid and a silicone resin; said composition also containing a sufficient quantity of at least one compound of the group consisting of an alkaline phosphate, a lower carboxylic acid and phenol so as to ensure said composition has a pH in the range 5 to 7.

8. A process for preserving fresh, naturally coloured blooms as claimed in claim 7, wherein said composition consists essentially of at least one dehydrating alcohol, thiourea, an alkaline phosphate, citric acid, an alkaline citrate, a silicone fluid and an effective amount of at least one of: aluminum sulphate, cupric sulphate, an alkaline formaldehyde sulphoxalate and phenol and zero to an effective amount of a silicone resin, and including immersion for a period of time sufficient to effect substantially complete dehydration, and subsequent drying at substantially room temperature.

9. A process for preserving fresh, naturally coloured blooms as claimed in claim 8 wherein said blooms are immersed in a composition consisting of:
- 175–575 ml. tertiary butyl alcohol
- 100–300 ml. 1-propanol
- 200–400 ml. 2-propanol
- 6–8 g. sodium phosphate
- 2–3 g. sodium formaldehyde sulphoxalate
- 2.5–7.5 g. citric acid
- 10–20 g. thiourea
- 2.5–10 g. aluminum sulphate
- 3–12 g. sodium citrate
- 0.5–2 g. cupric sulphate
- 10–200 ml. silicone fluid
- 0–50 ml. silicone resin, and
- 37–62 ml. phenol.

10. A process as claimed in claim 9 wherein a substantially transparent moisture resistant resinous coating is applied to said blooms after drying.

11. A process as claimed in claim 8 wherein said composition has a pH in the range 6.0–6.5.

12. A process as claimed in claim 8 wherein said composition contains:
- 375 ml. tertiary butyl alcohol
- 200 ml. 1-propanol
- 300 ml. 2-propanol
- 12 g. sodium phosphate
- 2 g. sodium formaldehyde sulphoxalate
- 5 g. citric acid
- 10 g. thiourea
- 5 g. aluminum sulphate
- 6 g. sodium citrate
- 1 g. cupric sulphate
- 63 ml. silicone fluid
- 25 ml. silicone resin, and
- 37 ml. phenol.

13. A composition as claimed in claim 1 wherein said silicone fluid is selected from Microfil ® MV-diluent and dimethyl siloxane.

14. A flower treated with a composition as claimed in claim 1.

15. A flower preserved according to the process as claimed in claim 8.

16. A composition of matter, for admixture with a dehydrating alcohol for the preservation of fresh, naturally coloured blooms, consisting essentially of a urea-containing compound, a carboxylic acid, an alkaline citrate, and an effective amount of at least one of aluminum and magnesium sulphate, a transitional metal sulphate, an alkaline formaldehyde sulfoxylate and from zero to an effective amount of a silicone fluid and a silicone resin and a sufficient quantity of at least one compound selected from the group consisting of an alkaline phosphate, a lower carboxylic acid and phenol to ensure a pH of 5 to 7.

* * * * *